United States Patent [19]
Lochhead et al.

[11] Patent Number: 5,985,840
[45] Date of Patent: Nov. 16, 1999

[54] SURFACTANTS FORMED FROM MENHADEN FISH

[75] Inventors: Robert Y Lochhead; Robert Bateman; Monica Tisack, all of Hattiesburg, Miss.; Mikhail Gololobov, Oak Park, Ill.

[73] Assignee: University of Southern Mississippi, Hattiesburg, Miss.

[21] Appl. No.: 08/846,103

[22] Filed: May 1, 1997

Related U.S. Application Data

[60] Provisional application No. 60/016,343, May 1, 1996.

[51] Int. Cl.$^6$ ..................................................... A61K 38/00
[52] U.S. Cl. ............................ 514/21; 530/344; 530/427; 530/412
[58] Field of Search ................................ 514/21; 530/344, 530/427, 412

[56] References Cited

U.S. PATENT DOCUMENTS 4,216,239  8/1980  Groppestad .
4,874,629  10/1989  Chang et al. .

*Primary Examiner*—Cecilia J. Tsang
*Assistant Examiner*—Patrick R. Delaney
*Attorney, Agent, or Firm*—Arnold White & Durkee

[57] ABSTRACT

Protein surfactants are recovered from processed menhaden fish. Stick water is clarified and soluble proteins contained therein are precipitated by the addition of ammonium sulfate. The precipitated proteins are recovered from the solution.

13 Claims, 3 Drawing Sheets

SURFACTANTS FORMED FROM MENHADEN FISH

This application claims the benefit of U.S. Provisional Application No. 60/016,343 filed May 1, 1996.

BACKGROUND OF THE INVENTION

The present invention relates to surfactants. More particularly, the present invention relates to fish proteins which can be used as surfactants.

Surfactants are used as dispersants, emulsifiers, foaming agents, wetting agents, and spreading agents. Surfactants are amphipathic molecules. The word amphipathic comes from the Greek, amphi meaning dual and Pathos meaning suffering. Thus an amphipatic molecule is a molecule which "suffers" both oil and water phases. Amphipathic molecules consist of a hydrophobic portion and a hydrophilic portion; typical examples are stearic acid and lauryl alcohol. Surfactants are used as wetting and spreading agents in commercial applications such as enhanced oil recovery, dispersion of powders in liquids, application of agricultural sprays and cosmetics.

The term wetting is often used loosely, but in fact there are three distinct types of wetting, designated adhesional wetting, spreading wetting, and immersional wetting. These may be better understood by considering the stages involved in immersing a solid cube, of side 1 cm, into a liquid.

Adhesional wetting occurs when the first face of the cube comes into contact with the liquid surface. The isothermal work associated with this process if given by $$Wa = \gamma_{s/l} - (\gamma_{s/v} + \gamma_{l/v}) \tag{1}$$

where $\gamma_{s/l}$, $\gamma_{s/v}$ and $\gamma_{l/v}$ are the interfacial free energies associated with the solid/liquid, solid/vapor and liquid/vapor interfaces respectively, and Wa is the work of adhesion of the liquid to the solid.

Immersional wetting occurs as the sides of the cube become submerged. As this happens, the solid vapor interface is directly exchanged for an equivalent area of solid/liquid interface. In this case:

$$Wi = \gamma_{s/l} - \gamma_{s/v} \tag{2}$$

Spreading wetting takes place when a drop of liquid spreads over a plane solid surface such as when the top surface of the cube is submerged. When this happens a solid/vapor interface is replaced by equal areas of solid/liquid and liquid/vapor interfaces.

The work of spreading, therefore, can be equated to the relevant interfacial free energies:

$$Ws = (\gamma_{s/l} + \gamma_{l/v}) - \gamma_{s/v} \tag{3}$$

Values of $\gamma_{s/v}$ and $\gamma_{s/l}$ are not readily accessible by experiment, but they are related by the Young-Dupré equation for contact-angle of a liquid drop on a solid surface measured through the liquid. The Young-Dupré equation is $$\gamma_{s/v} = \gamma_{s/l} + \gamma_{l/v} \cos\theta \tag{4}$$

Substituting equation (4) into equations (1), (2), and (3) gives $$Wa = \gamma_{s/l} - (\gamma_{l/v} + \gamma_{s/v}) = -\gamma_{l/v}(\cos\theta + 1) \tag{5}$$

$$Wi = \gamma_{s/l} - \gamma_{s/v} = -\gamma_{l/v} \cos\theta \tag{6}$$

$$Ws + (\gamma_{s/l} + \gamma_{l/v}) - \gamma_{s/v} = -\gamma_{l/v}(\cos\theta - 1) \tag{7}$$

For a spontaneous process to occur, W must be negative. Therefore:

(i) Adhesional wetting occurs (Wa is negative) regardless of the value of $\cos\theta$. That is, adhesional wetting is always spontaneous.

(ii) Spreading wetting occurs only when $\cos\theta = 1$. That is, when $\theta = 0°$.

(iii) Immersional wetting occurs and immersion is spontaneous when $\theta$ lies between 0° and 90°.

When an aggregate is introduced to a liquid, if the contact-angle of the liquid on the solid is less than 90°, the spontaneous immersional wetting will occur. In order to decrease the aggregate size without exerting an inordinate amount of mechanical shear, however, the liquid must penetrate the pore structure of the aggregate and this can be achieved only by spreading wetting, with a contact-angle of 0.

Factors which are important in forcing liquid into the channels between and inside agglomerates cannot be precisely defined, but the important parameters can be elucidated by considering the pressure (P) required to force liquid into a capillary of radius, r:

$$P = -2\gamma_{l/v} \cos\theta / r \tag{8}$$

Substituting from equation (4)

$$P = -2(\gamma_{s/v} - \gamma_{s/l})/r \tag{9}$$

Therefore, for penetration to proceed $\gamma_{s/l}$ should be made as small as possible. If the liquid spreads into the pores, then, from equation (6), $\theta$ should be zero. However, if $\theta$ is zero, equation (8) becomes $$P = -2\gamma_{l/v}/r \tag{10}$$

Therefore, for penetration to occur $\gamma_{l/v}$ should be as large as possible. However, most surfactants lower both $\gamma_{l/v}$ and $\gamma_{s/l}$ simultaneously. The rate of penetration is also an important factor. This rate is defined by the Washburn equation, which for a packed bed of porous particles becomes $$l^2 = \frac{Kr\gamma_{l/v}\cos\theta}{2\eta} \tag{11}$$

where 1 is a depth of penetration in time t, $\eta$ is the liquid viscosity, and K is a factor which defines the equivalent "capillarity" of the bed.

Equation (11), therefore, tells us that for fastest penetration, sufficient surfactant should be added to decrease the contact-angle, $\theta$, to zero. Addition of further surfactant will reduce $\gamma_{l/v}$ while $\cos\theta$ will remain at unity. This means that adding excess surfactant will actually reduce the rate of penetration of the liquid into the pores.

Surfactants are generally divided into four classes: amphoteric, with zwitterionic head groups; anionic, with negatively charged head groups; cationic, with positively charged head groups; and nonionic, with uncharged hydrophilic head groups. Anionic surfactants include long-chain fatty acids, sulfosuccinates, alkyl sulfates, phosphates, and sulfonates. Cationic surfactants include protonated long-chain amines and long-chain quaternary ammonium compounds. Amphoteric surfactants include betaines and certain lecithins. Nonionic surfactants include polyethylene oxide, alcohols, and other polar groups.

Because of their many uses and potential uses, it would be an advancement in the art to provide a novel source of surfactants that could be produced economically. It would be a further advancement if those surfactants had unique properties. Such surfactants are disclosed and claimed herein.

SUMMARY OF THE INVENTION

The present invention relates to surfactants formed from proteins isolated from menhaden fish. In a preferred embodiment, stick water from processed menhaden fish is clarified by centrifugation. The clarified water is then fractionated by the addition of ammonium sulfate to a concentration of about 60% of saturation. The proteins precipitated by the addition of the ammonium sulfate are recovered and form an excellent surfactant.

In one preferred embodiment, the recovered proteins are redissolved in distilled water to a final protein concentration of about 1%. This solution is then frozen quickly and the supernatant is lyophilized. The recovered protein fraction can then be stored in a sealed, dessicated container for later use as a surfactant.

DETAILED DESCRIPTION OF THE PREFERRED EMBODIMENTS

Figure 1:
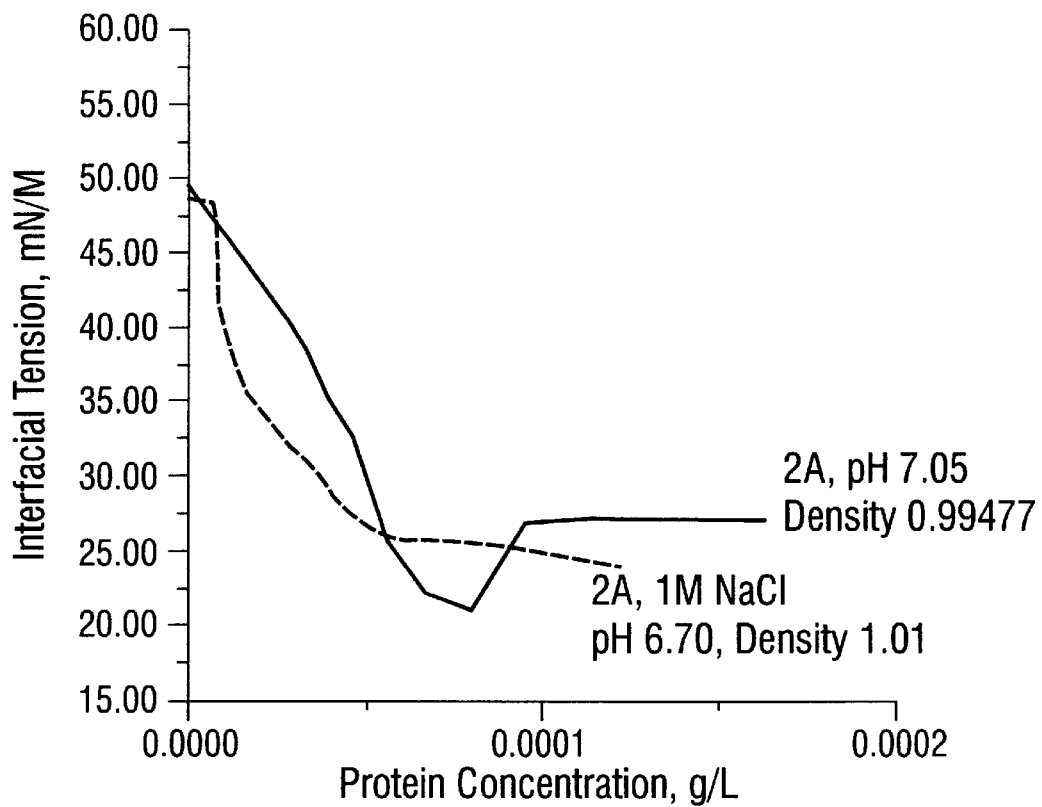
FIG. 1 and FIG. 2 are graphs showing interfacial tension measurements using the surfactants of the present invention.

The present invention involves proteins isolated from menhaden fish byproducts which can be used as surfactants. Currently, menhaden fish are primarily processed for their oil. The proteins remaining after the oil has been removed are used in poultry, swine, and catfish feeds. The soluble protein products created from these processes comprise tens of millions of pounds per year.

During the processing of menhaden fish to obtain oil, certain by-products are produced. Generally, the fish are boiled, compressed and then filtered. The filtering process produces "press cake" and "stick water." The press cake comprises water and soluble material composed primarily of protein with very little fat. Stick water represents the aqueous liquor remaining after nearly all of the oil and solids have been removed. It contains a mixture of proteins, biogenic amines (amino acid decomposition products), lipids and a certain amount of the insoluble material which is left due to its incomplete separation from the liquor during filtering.

In a preferred embodiment of the present invention, soluble proteins are recovered from the stick water obtained by processing menhaden fish. First, all remaining insoluble components are removed from the stick water. This can be accomplished by centrifugation. In one embodiment, the stick water is centrifuged at 15,000×g for 20 minutes at room temperature. Other processes of removing insoluble components can also be used and are well known to those skilled in the art. Processing of the stick water and proteins is generally performed at room temperature because of the tendency of the solution to gel at lower temperatures.

The solution is then fractionated to recover the protein. In one embodiment, ammonium sulfate is added to the solution to precipitate the protein. Most of the protein can be precipitated at an ammonium sulfate concentration of about 60% of saturation or about 3M. Lesser concentrations recover less protein but greater concentrations do not generally produce a significant increase in the amount of recovered proteins. It is of importance to note that primary aliphatic amines should be soluble at any concentration of ammonium sulfate. Therefore, most amines (i.e., compounds with an offensive smell) stay in the supernatant during the salting-out procedure and can be removed by simple decantation.

Other soluble salts such as sodium sulfate can be used in the present invention provided they do not degrade the proteins.

The precipitated protein is separated from the solution by centrifugation or any other suitable separation process. This recovered protein has excellent surface-active properties making it an extraordinary surfactant.

The proteins can be further processed to increase their purity if desired. For example, some of the salt can be removed by dialysis. However, it has been found that this is generally not necessary.

The proteins can also be further processed to make them easier to store and transport. For example, the proteins can be dried and stored in a sealed, dessicated container. In one embodiment, the precipitated protein is dissolved in distilled water to a final protein concentration of about 1%, rapidly frozen, and the supernatant lyophilized. In a preferred embodiment, a dry ice/acetone bath is used to freeze the protein.

The proteins of the present invention are amphipathic molecules and they can adsorb at both an air/liquid interface and an oil/water interface. However, it has been discovered that these proteins preferentially adsorb at the oil/water interface rather than the air/water surface.

The properties and features of the present invention can be more fully understood by reference to the following examples.

EXAMPLE 1

Isolation of Protein

To obtain a solution of protein free of contaminants and ready for fractionation, stick water from gulf menhaden fish from the 1995 season was centrifuged at 15,000×g for 20 minutes at room temperature and separated. This removed all dispersed, but insoluble components. All operations had to be carried out at room temperature because of the tendency of the solution to gel at lower temperatures.

A portion of the clarified protein solution was then fractionated by adding ammonium sulfate to a concentration of about 60% of saturation, or about 3M. This resulted in most of the protein being precipitated which was then recovered by centrifugation. The precipitated protein was dissolved in distilled water to a final protein concentration of approximately 1%, frozen quickly in a dry ice/acetone bath and the supernatant was lyophilized. The protein fraction obtained by this process was a light tan, spongy solid and was referred to as Fraction 2A.

Since the molar concentration of ammonium sulfate at 60% of saturation (3 M) is much higher than the protein concentration, the protein pellet obtained after centrifugation contains an uncontrolled amount of entrapped salt. In order to determine the effect of this salt on the surfactant, another portion of clarified protein solution was fractionated by adding ammonium sulfate. The precipitated protein was recovered by centrifugation. This protein was redissolved and some of the salt was removed from this solution by extensive dialysis against distilled water. This procedure resulted in precipitation of some proteins which apparently were not soluble in the lowered ionic strength. This precipitated protein was removed by centrifugation. The remaining solution was lyophilized to a spongy protein solid as described above. This "salt-free" fraction was referred to as Fraction 2B.

Both Fractions 2A and 2B are extremely hygroscopic and require storage in sealed, dessicated containers.

EXAMPLE 2

Determination of Interfacial Tension

A Kruss K12 tensiometer was used to determine the interfacial tension of Fractions 2A and 2B at a cyclohexane/water interface. These measurements were taken using the DeNouy ring method. Interfacial tension measurements of the fish proteins were taken with and without 1 M NaCl added to the solutions.

Figure 2:
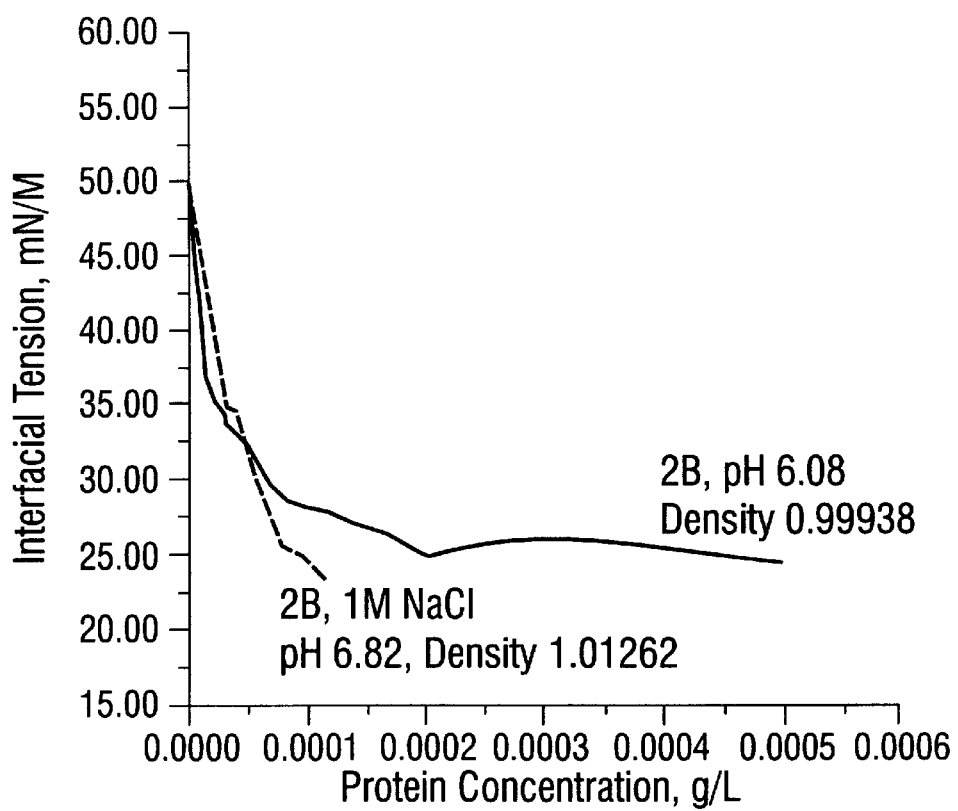

The results of the interfacial tension measurements are illustrated in FIGS. 1 and 2. As can be seen in FIG. 1, when salt is added, there is generally a greater reduction in the interfacial tension at the same protein concentration. Comparing FIG. 1 and FIG. 2 shows that both fractions provide a substantial reduction in the interfacial tension at an oil/water interface.

EXAMPLE 3

Determination of Viscosity

Figure 3:
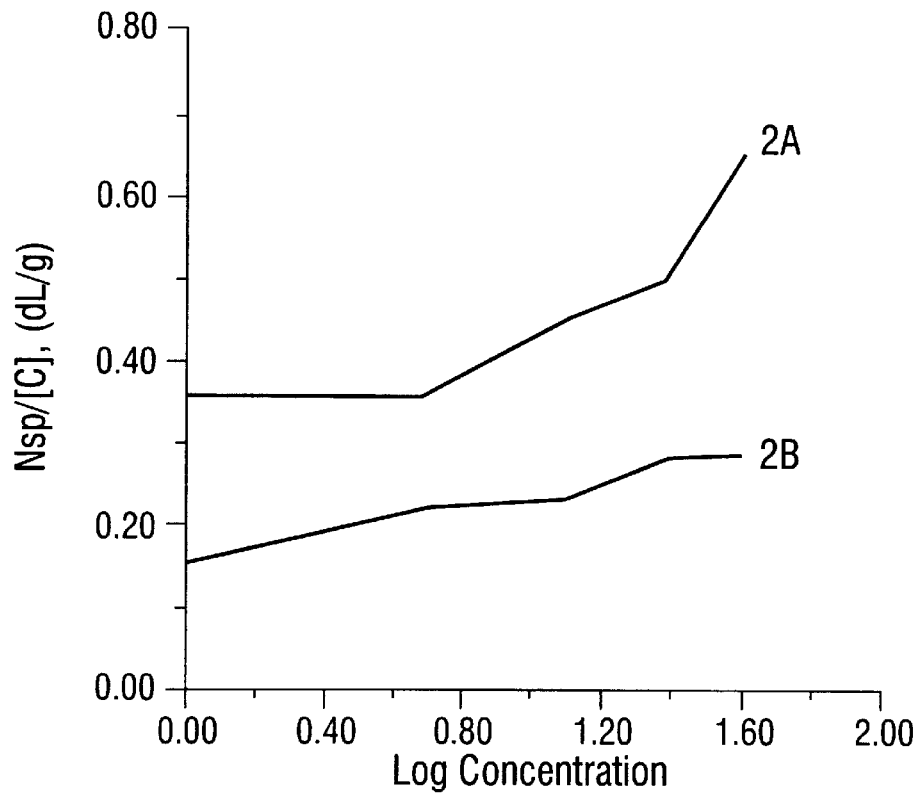
FIG. 3 is a graph of the viscosities of solutions containing the surfactants of the present invention.

A Contraves Low Shear 30 viscometer was used to obtain viscosities for the fractions obtained in Example 1. The results are illustrated in FIG. 3. The concentrations required to produce any significant change in viscosity were so high that all of the fish protein would not go into solution. In FIG. 3, the increase in the slope of Batch 2A at 1.4 was due to solid particles in the sample which were not in solution.

EXAMPLE 4

Determination of Surface Tensions

Figure 4:
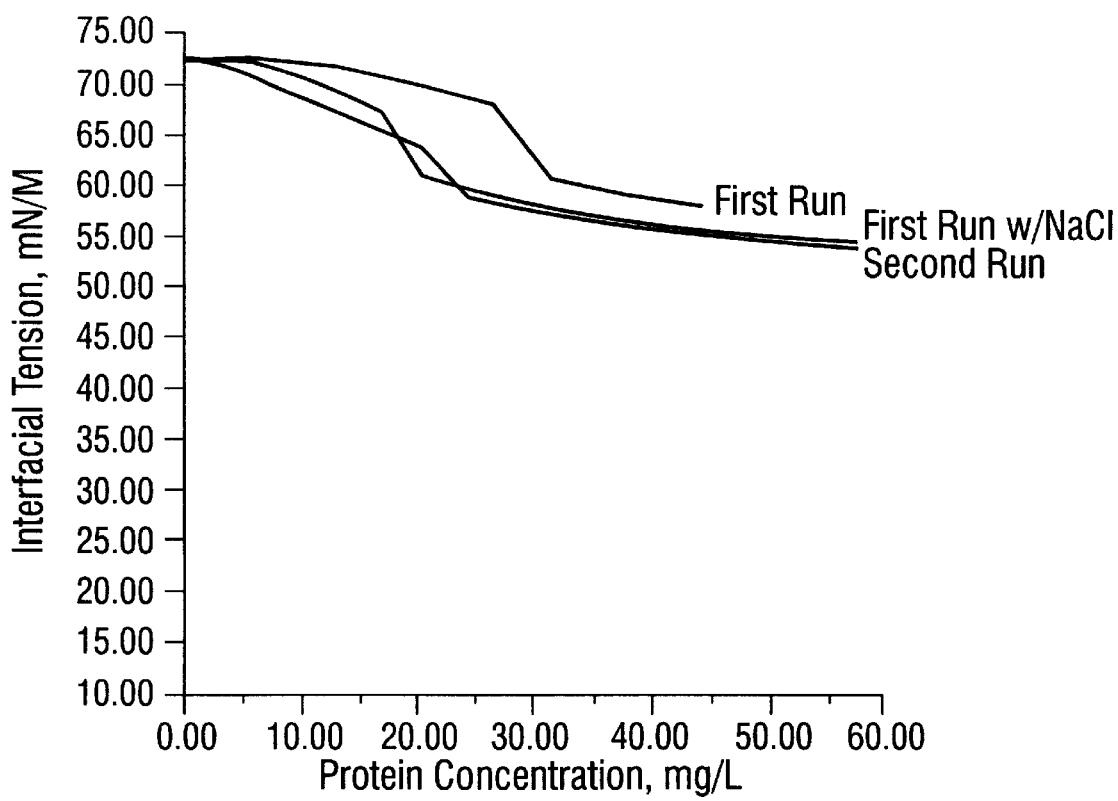
FIG. 4 is a graph of surface tension measurements using the surfactants of the present invention.

Stick water from another batch of menhaden fish from the 1995 gulf season was processed as described in Example 1 for fraction 2A to obtain a protein fraction referred to as batch 3A. Surface tension measurements of batch 3A were taken at an air/water interface using a Wilhelmy plate and a Kruss K12 tensiometer. Measurements were taken with and without 1M NaCl. The results are illustrated in FIG. 4. As can be seen by examining FIG. 4, significant protein concentrations were required to obtain a decrease in the surface tension.

EXAMPLE 5

Tension Measurements for Various Cuts

A series of experiments were conducted to determine whether various cuts of the proteins recovered from the stick water from menhaden fish produced different results.

A portion of batch 3A was redissolved in distilled water to a final protein concentration of 1%. Ammonium sulfate was gradually added to this solution to reprecipitate the proteins. When the solution was 20% saturated with ammonium sulfate, the proteins were separated from the solution and were designated as the 0–20% cut. Additional ammonium sulfate was added to the remaining solution to precipitate additional protein. When the solution was 40% saturated, the protein was separated and designated as the 20–40% cut. Additional ammonium sulfate was then added to reach a 60% saturation level. The protein was again recovered and designated as the 40–60% cut.

These three cuts were then tested with and without salt being added to determine interfacial tensions and surface tensions according to the procedures described in Examples 2 and 4. The results of these tests are illustrated in FIG. 5.

Figure 5:
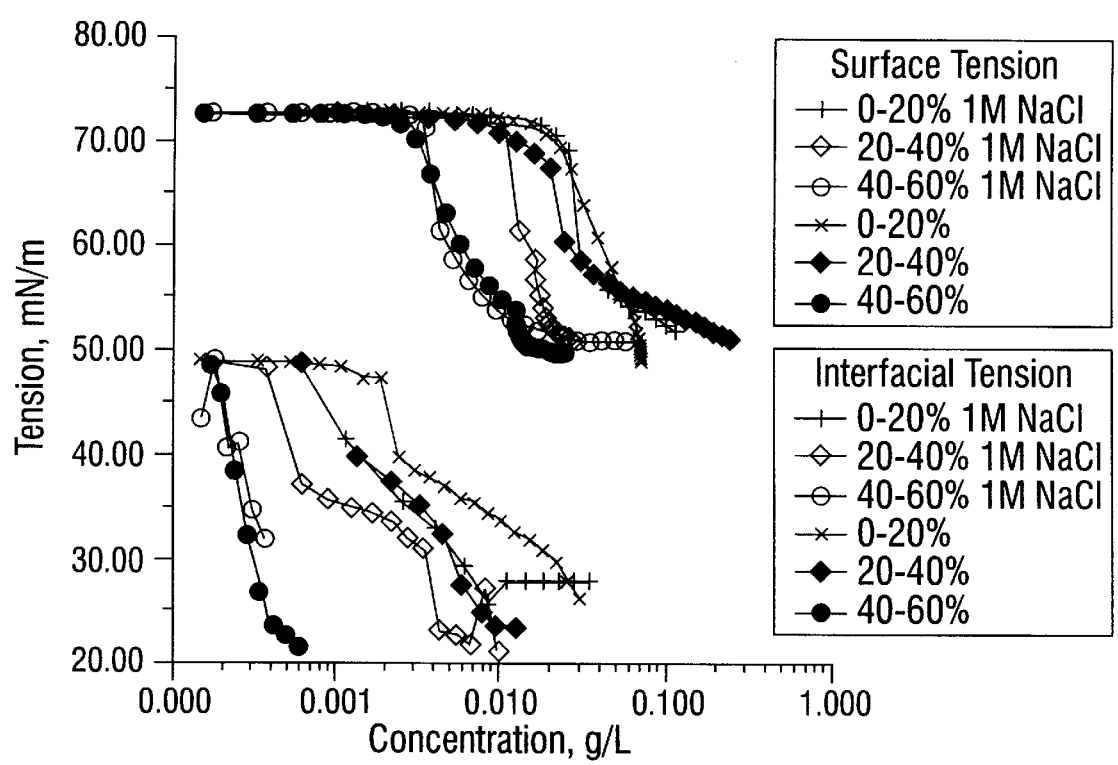
FIG. 5 is a graph of surface and interfacial tension measurements of various cuts of the surfactants of the present invention.

As can be seen from examining FIG. 5, the second cut resulted in slightly lower tension measurements than did the first cut and the third cut resulted in slightly lower tension measurements than did the second cut. However, the difference between the surface tension and the interfacial tension for the various cuts appears to have remained generally the same.

As can be seen from the foregoing, the soluble proteins obtained from menhaden fish are excellent surfactants. They preferentially adsorb at the oil/water interface. Additionally, only small amounts are required to lower the interfacial tension of an oil/water mixture. Further, these surfactants are readily biodegradable as compared to many synthetic surfactants.

While the invention has been described with respect to the presently preferred embodiments, it will be apparent to those skilled in the art that various changes can be made to the preferred embodiments without departing from the spirit or scope of the invention. For example, other salts can be used to precipitate the proteins and other separation processes can be used to separate the precipitate from the solution. Accordingly, the scope of the invention is defined by the appended claims rather than by the foregoing description and all changes or modifications which come within the meaning and range of the claims are to be embraced within their scope.

What is claimed is:

1. A surfactant comprising soluble proteins extracted from menhaden fish by obtaining stick water from processed menhaden fish and fractionating said water to recover dissolved proteins which are surfactants.

2. A surfactant as defined in claim 1 wherein dispersed but insoluble components are removed from said stick water prior to fractionating said water.

3. A surfactant as defined in claim 1 wherein said fractionating step comprises precipitating said proteins.

4. A surfactant as defined in claim 3 wherein said proteins are precipitated with ammonium sulfate.

5. A surfactant as defined in claim 3 further comprising washing said precipitated proteins.

6. A surfactant comprising soluble proteins recovered from menhaden fish according to the process of claim 1.

7. A process for producing surfactants comprising:

obtaining stick water from processed menhaden fish; and fractionating said water to recover dissolved proteins which are surfactants.

8. A process for producing surfactants as defined in claim 7 further comprising freeze drying said proteins.

9. A process for producing surfactants as defined in claim 7 wherein said fractionating step comprises precipitating said proteins.

10. A process for producing surfactants as defined in claim 9 wherein said proteins are precipitated with ammonium sulfate.

11. A process for producing surfactants as defined in claim 10 further comprising washing said precipitated proteins.

12. A process for producing surfactants as defined in claim 7 further comprising processing menhaden fish to obtain stick water.

13. A process for producing surfactants as defined in claim 7 further comprising removing dispersed from insoluble components from said water prior to fractionating said water.

* * * * *

UNITED STATES PATENT AND TRADEMARK OFFICE
CERTIFICATE OF CORRECTION

PATENT NO. : 5,985,840
DATED : November 16, 1999
INVENTOR(S) : Robert Y. Lochhead, et al.

It is certified that error appears in the above-identified patent and that said Letters Patent is hereby corrected as shown below:

Column 1, line 67 delete duplicate "$\gamma_{s/v}$" in equation (7)

Signed and Sealed this

Fifth Day of September, 2000

Attest:

Q. TODD DICKINSON

Attesting Officer

Director of Patents and Trademarks